(12) United States Patent
Tan et al.

(10) Patent No.: US 9,255,065 B1
(45) Date of Patent: Feb. 9, 2016

(54) MULTI(AZOBENZENE-AMINE) PHOTOACTIVE CROSSLINKERS AND METHODS OF MAKING THE SAME

(71) Applicant: The United States of America, as represented by the Secretary of the Air Force, Washington, DC (US)

(72) Inventors: Loon-Seng Tan, Centerville, OH (US); David Huabin Wang, Beavercreek, OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 389 days.

(21) Appl. No.: 13/866,524

(22) Filed: Apr. 19, 2013

Related U.S. Application Data

(60) Provisional application No. 61/636,134, filed on Apr. 20, 2012, provisional application No. 61/636,170, filed on Apr. 20, 2012.

(51) Int. Cl.
*C07C 245/08* (2006.01)

(52) U.S. Cl.
CPC .................................... *C07C 245/08* (2013.01)

(58) Field of Classification Search
CPC .................................................... C07C 245/08
See application file for complete search history.

(56) References Cited

U.S. PATENT DOCUMENTS

| | | | |
|---|---|---|---|
| 3,455,879 A | 7/1969 | Gay et al. | |
| 3,514,415 A | 5/1970 | Karol | |
| 3,600,361 A | 8/1971 | Heacock et al. | |
| 3,732,200 A | 5/1973 | Bach | |
| 3,763,211 A | 10/1973 | Heath et al. | |
| 3,835,120 A | 9/1974 | Bach et al. | |
| 3,925,312 A | 12/1975 | Fletcher | |
| 3,988,374 A | 10/1976 | Brode et al. | |
| 4,107,125 A | 8/1978 | Lovejoy | |
| 4,111,906 A | 9/1978 | Jones et al. | |
| 4,203,922 A | 5/1980 | Jones et al. | |
| 4,271,288 A | 6/1981 | Woo | |
| RE30,922 E | 5/1982 | Heilman et al. | |
| 4,394,499 A | 7/1983 | Robinson et al. | |
| 4,535,101 A | 8/1985 | Lee et al. | |
| 4,728,697 A | 3/1988 | Bolon et al. | |
| 4,797,466 A | 1/1989 | Oikawa et al. | |
| 4,981,497 A | 1/1991 | Hayes | |
| 5,101,005 A | 3/1992 | Vora et al. | |
| 5,101,037 A | 3/1992 | McGrath et al. | |
| 5,175,234 A | 12/1992 | Lubowitz et al. | |
| 5,205,894 A | 4/1993 | Ohta et al. | |
| 5,278,276 A | 1/1994 | Ohta et al. | |
| 5,300,559 A | 4/1994 | Sheehan et al. | |
| 5,344,894 A | 9/1994 | Lubowitz et al. | |
| 5,411,765 A | 5/1995 | Kanakarajan et al. | |
| 5,508,377 A | 4/1996 | Yamashita et al. | |

(Continued)

FOREIGN PATENT DOCUMENTS

| | | |
|---|---|---|
| EP | 233069 | 8/1987 |
| EP | 333406 | 9/1989 |
| EP | 659802 | 6/1995 |
| EP | 397023 | 1/2009 |
| EP | 2380867 | 10/2011 |
| GB | 1147856 | 4/1969 |
| JP | 2005023151 | 1/2005 |
| JP | 2005154643 A | 6/2005 |
| JP | PCTJP2007051217 | 2/2007 |
| SE | EP 2 380 867 A1 | 4/2010 |
| WO | 2009013376 | 1/2009 |

OTHER PUBLICATIONS

Wang, David H. Photomechanical Response of Glassy Azobenzene Polyimide Networks. Macromolecules. 2011, 44, 3840-3846.*

(Continued)

*Primary Examiner* — Samantha Shterengarts
(74) *Attorney, Agent, or Firm* — AFMCLO/JAZ; Chastity Whitaker

(57) ABSTRACT

Photo-active cross-linkers derived from a tris(azobenzene)-containing compound with the following generic structure:

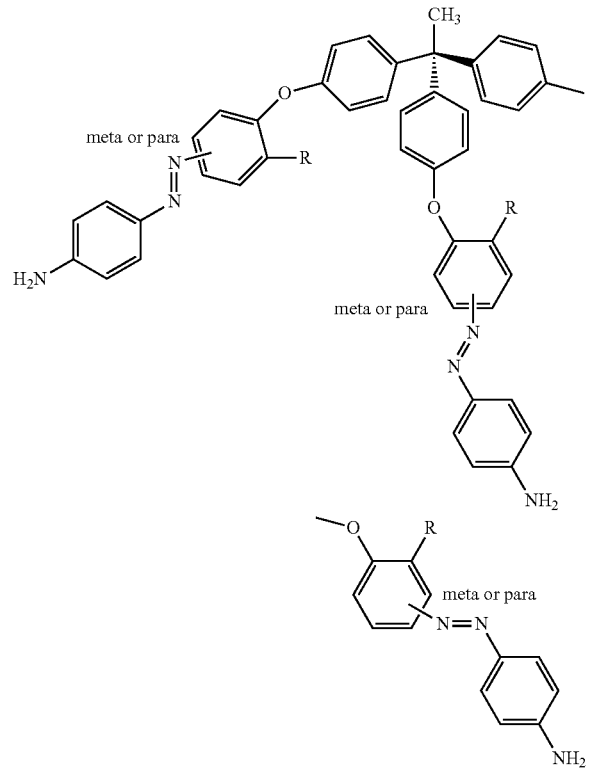

wherein for meta-azo substitution, R is equal to H, and for para-azo substitution, R is selected from the group consisting of H, F, Cl, $CF_3$, and $CH_3$.

7 Claims, 2 Drawing Sheets

(56) References Cited

U.S. PATENT DOCUMENTS

| | | | |
|---|---|---|---|
| 5,516,876 | A | 5/1996 | Lubowitz et al. |
| 5,585,217 | A | 12/1996 | Oba |
| 5,599,582 | A | 2/1997 | Adamopoulous et al. |
| 5,610,265 | A | 3/1997 | Tan et al. |
| 5,631,377 | A | 5/1997 | Matsuo et al. |
| 5,670,651 | A | 9/1997 | Tan et al. |
| 5,705,574 | A | 1/1998 | Lubowitz et al. |
| 5,891,581 | A | 4/1999 | Simpson et al. |
| 5,965,687 | A | 10/1999 | Jensen |
| 6,001,277 | A | 12/1999 | Ichimura et al. |
| 6,184,333 | B1 | 2/2001 | Gray |
| 6,262,223 | B1 | 7/2001 | Meador et al. |
| 6,307,008 | B1 | 10/2001 | Lee et al. |
| 6,379,809 | B1 | 4/2002 | Simpson et al. |
| 6,509,094 | B1 | 1/2003 | Shah et al. |
| 7,402,264 | B2 | 7/2008 | Ounaies et al. |
| 7,507,472 | B2 | 3/2009 | Ounaies et al. |
| 7,527,751 | B2 | 5/2009 | Ounaies et al. |
| 7,582,722 | B1 | 9/2009 | Tan et al. |
| 7,588,699 | B2 | 9/2009 | Park et al. |
| 7,678,873 | B1 | 3/2010 | Tan et al. |
| 7,906,043 | B2 | 3/2011 | Connell et al. |
| 7,935,414 | B2 | 5/2011 | Ounaies et al. |
| 7,972,536 | B2 | 7/2011 | Connell et al. |
| 8,034,893 | B2 | 10/2011 | Akiba et al. |
| 8,173,763 | B1 | 5/2012 | Tan et al. |
| 8,314,203 | B2 | 11/2012 | Tsutsumi et al. |
| 8,389,619 | B1 | 3/2013 | Tan et al. |
| 8,546,614 | B1 | 10/2013 | Tan et al. |
| 8,633,284 | B2 | 1/2014 | Ronk et al. |
| 8,785,589 | B1 | 7/2014 | Tan et al. |
| 8,791,227 | B1 | 7/2014 | Tan et al. |
| 2003/0064235 | A1 | 4/2003 | Okawa et al. |
| 2004/0233377 | A1 | 11/2004 | Utsumi et al. |
| 2005/0080229 | A1 | 4/2005 | Deets et al. |
| 2006/0057377 | A1 | 3/2006 | Harrison et al. |
| 2006/0217482 | A1 | 9/2006 | Lukehart et al. |
| 2006/0235194 | A1 | 10/2006 | Kato |
| 2006/0270825 | A1 | 11/2006 | Angermeier et al. |
| 2007/0106056 | A1 | 5/2007 | Itatani |
| 2007/0270562 | A1 | 11/2007 | Yamada et al. |
| 2007/0272124 | A1 | 11/2007 | Tsutsumi et al. |
| 2008/0025905 | A1 | 1/2008 | Wang et al. |
| 2008/0311303 | A1 | 12/2008 | Naiki et al. |
| 2009/0220722 | A1 | 9/2009 | Wang |
| 2010/0048745 | A1 | 2/2010 | Yamada et al. |
| 2011/0009513 | A1 | 1/2011 | Chaudhary et al. |
| 2011/0136061 | A1 | 6/2011 | Itatani |

OTHER PUBLICATIONS

U.S. Patent and Trademark Office, Non-Final Office Action mailed Sep. 26, 2012, U.S. Appl. No. 13/557,326, 9 pages.

U.S. Patent and Trademark Office, Non-Final Office Action mailed Mar. 27, 2013, U.S. Appl. No. 13/557,326, 5 pages.

U.S. Patent and Trademark Office, Non-Final Office Action mailed Nov. 7, 2013, U.S. Appl. No. 13/546,439, 9 pages.

Meador, Mary Ann B., et al., "Synthesis and Properties of Nanoporous Polyimide Aerogels Having a Covalently Bonded Network Structure," Polymer Preprints 2010, 51(1), 265.

Japanese Patent Office, Machine Translation of JP 2005154643A, 39 pages.

Meador, Mary Ann B., et al., "Improvements to the Synthesis of Polyimide Aerogels," ACS Spring National Meeting 2011, Anaheim, CA; Mar. 20-26, 2011, 34 pages.

Jenekhe, Samson A. et al., Nonlinear Optical Properties of Poly(p-phenylenebenzobisoxazole), Chem. Mater. 1992, 4, 683-687.

Kannan, Ramamurthi, et al., Diphenylaminofluorene-Based Two-Photon Absorbing Chromophores with Various π-Electron Acceptors, Chem. Mater. 2001, 13, 1896-1904.

Pyun, Eumi, et al., "Kinetics and mechanisms of thermal imidization of a polyamic acid studied by ultraviolet-visible spectroscopy", Macromolecules (1989), 22(3), 1174-83.

Natansohn, A., et al., "Photoinduced Motions in Azo-Containing Polymers," Chemical Reviews (Washington, DC, United States) (2002), 102(11), 4139-4175.

Hugel, Thorsten, et al., "Single-molecule optomechanical cycle", Science (2002), 296(5570), 1103-1106.

Hosono, Nobuhiko, et al., "Photochemical control of network structure in gels and photo-induced changes in their viscoelastic properties" Colloids and Surfaces, B: Biointerfaces (2007), 56(1-2), 285-289.

Zhang, Chaohui, et al., "Rapid bending of a nonliquid crystal azobenzene polymer film and characteristics of surface relief grating" Journal of Applied Polymer Science (2009), 113(2), 1330-1334.

Kannan, Ramamurthi, et al., "Toward Highly Active Two-Photon Absorbing Liquids: Synthesis and Characterization of 1,3,5-Triazine-Based Octupolar Molecules," Chem. Mater. 2004, 16, 185-194.

He, Guang S., et al., "Degenerate Two-Photon-Absorption Spectral Studies of Highly Two-Photon Active Organic Chromophores," J. Chem. Phys., vol. 120 No. 11 (2004) 5275-5284.

Wang, David H., et al., "Photomechanical Response of Glassy Azobenzene Polyimide Networks" Macromolecules 2011, 44, pp. 3840-3846.

Hrozhyk, Uladzimir, et al., "Bidirectional Photoresponse of Surface Pretreated Azobenzene Liquid Crystal Polymer Networks," Optics Express, vol. 17, Issue 2, pp. 716-722 (2009).

Usami, Kiyoaki, et al., "Photo-Aligned Blend Films of Azobenzene-Containing Polyimides with and without Side-Chains for Inducing Inclined Alignment of Liquid Crystal Molecules," Journal of Applied Physics (2011), 110(4), 043522/1-043522/6.

Makita, Shohei, et al., "Synthesis of Alkaline-Developable, Photosensitive Hyperbranched Polyimides through the Reaction of Carboxylic Acid Dianhydrides and Trisamines," Journal of Polymer Science Part A: Polymer Chemistry, vol. 42, 3697-3707 (2004).

Lendlein Andreas et al., "Shape-Memory Polymers," Angewandte Chemie, International Edition, vol. 41, 2034-2057 (2002).

Liu C. et al., "Review of Progress in Shape-Memory Polymers," Journal of Materials Chemistry, vol. 17, 1543-1558 (2007).

Fay, Catherine C. et al., "Molecularly Oriented Polymeric Thin Films for Space Applications," High Performance Polymers, vol. 11, 145-156 (1999).

SRS Technologies and Mantech Materials, "Polyimides: CP1 and CP2 Film Properties," printed Jul. 9, 2012, 1 page, available at <http://www.mantechmaterials.com/_images/documents/3_8_doc.pdf>.

St. Clair, Anne K., et al. "Synthesis and Characterization of Essentially Colorless Polyimide Films," J. Polym. Mater. Sci Eng., vol. 51, pp. 62-66 (1984).

Miner, Gilda A., et al., "The Wettability of LaRC Colorless Polyimide Resins on Casting Surfaces," J. Polym. Mater. Sci Eng., vol. 76, pp. 381-382 (1997).

Straub, Daniel, "Lewis Structures of Boron Compounds Involving Multiple Bonding," J. Chem. Ed. 72(6) 494-497 (1995).

Chao, Tsung-Yi, et al., "Nonlinear Optical Polyimide/Montmorillonite/Nanocomposites Consisting of Azobenzene Dyes," Dyes and Pigments, 77 (2008) 515-524.

Agolini, F., et al., "Synthesis and Properties of Azoaromatic Polymers," Macromolecules (May-Jun. 1970), vol. 3, No. 3, 349-351.

Lovrien, R., "The Photoviscosity Effect," Proc. Natl. Acad. Sci. U.S.A. 1967 (57) 236-242.

Cojocariu, C., et al., "Light-induced motions in azobenzene-containing polymers," Pure Appl. Chem. 2004, 76, 1479-1497.

Tabiryan, N., et al., "Polymer film with optically controlled form and actuation," T. Optics Express 2005, 13, 7442-7448.

White, T.J., et al., "A high frequency photodriven polymer oscillator," J. Soft Matter 2008,4, 1796-1798.

Barrett, C.J., et al., "Photo-mechanical effects in azobenzene-containing soft materials," Soft Matter 2007, 3, 1249-1261.

Park, C., et al., "Actuating Single Wall Carbon Nanotube—Polymer Composites: Intrinsic Unimorphs," Adv. Mater. 2008, 20, 2074-2079.

Van Oosten, C.L., et al., "Bending Dynamics and Directionality Reversal in Liquid Crystal Network Photoactuators," Macromolecules 2008,41,8592-8596.

(56) References Cited

OTHER PUBLICATIONS

Irie, M., "Photochromism and Molecular Mechanical Devices," Bull. Chem. Soc. Jpn. 2008, 81 (8), 917-926.
Serak, S.V., et al., "Azobenzene liquid crystal polymer-based membrane and cantilever optical systems," Optics Express, vol. 17, No. 18 (Aug. 31, 2009), 15736-15746.
Hogan, P.M., et al., "UV-Manipulation of Order and Macroscopic Shape in Nematic Elastomers," Phys. Rev. E: Stat., Nonlinear, Soft Matter Phys. 2002, 65, 041720/1-041720110.
Eisenbach, C.D., "Isomerization of aromatic azo chromophores in poly(ethyl acrylate) networks and photomechanical effect," Polymer 1980, 21, 1175-1179.
Viswanathan, N.K., et al., "Surface relief structures on azo polymer films," J. Mater. Chem. 1999, 9, 1941-1955.
Harris, K.D., et al., Large amplitude light-induced motion in high elastic modulus polymer actuators, J. Mater. Chem. 2005, 15, 5043-5048.
Van Oosten, C.L., et al., "Glassy photomechanical liquid-crystal network actuators for microscale devices," Eur. Phys. J. E, 2007, 23, 329-336.
White, T.J., et al., "Polarization-controlled, photodriven bending in monodomain liquid crystal elastomer cantilevers," J. Mater. Chem. 2009, 19, 1080-1085.
Lee, K.M., et al., "Relationship between the Photomechanical Response and the Thermomechanical Properties of Azobenzene Liquid Crystalline Polymer Networks," Macromolecules 2010, 43, 8185-8190.
Finkelmann, H., et al., "A New Opto-Mechanical Effect in Solids," Phys. Rev. Lett. 2001, 87, 01550111-01550114.
Sroog, C.E., "Polyimides," Prog. Polym. Sci. 1991, 16, 561-694.
Koshiba, Y., et al., "Photo-induced alignment behavior of azobenzene compound in thin film," Thin Solid Films 2009, 518, 805-809.
Koerner, H., et al., "Photogenerating work from polymers," Mater. Today (Oxford, U. K.) 2008, 11, (7-8), 34-42.
Wang, D.H., et al., "Nanocomposites Derived from a Low-Color Aromatic Polyimide (CP2) and Amine-Functionalized Vapor-Grown Carbon Nanofibers: In Situ Polymerization and Characterization," Macromolecules 2007, 40, 6100-6111.
Yu, Y., et al., "Photomechanical Effects of Ferroelectric Liquid-Crystalline Elastomers Containing Azobenzene Chromophores," Angew. Chem., Int. Ed. 2007, 46, 881-883.
Arlen, M., et al., "Thermal-Electrical Character of in Situ Synthesized Polyimide-Grafted Carbon Nanofiber Composites," Macromolecules 2008, 41, 8053-8062.
Chen, J.P., et al., "Highly Stable Optically Induced Birefringence and Holographic Surface Gratings on a New Azocarbazole-Based Polyimide," Macromolecules 1999, 32, 8572-8579.
Kumar, G.S., et al., "Photochemistry of Azobenzene-Containing Polymers," Chem. Rev. 1989, 89, 1915-25.
Yu, Y., et al., "Effect of Cross-linking Density on Photoinduced Bending Behavior of Oriented Liquid-Crystalline Network Films Containing Azobenzene," Chem. Mater. 2004, 16, 1637-1643.
Kondo, M., et al., "Effect of concentration of photoactive chromophores on photomechanical properties of crosslinked azobenzene liquid-crystalline polymers," J. Mater. Chem. 2010, 20, 117-122.
Li, M.-H., et al., "Light-Driven Side-On Nematic Elastomer Actuactors," Adv. Mater. 2003, 15, 569-572.
Amaranatha Reddy et al., "Occurance of the B7 mesophase in two homologous series of seven-ring achiral compounds composed of banana-shaped molecules," Liq. Cryst., vol. 30 (203) 273-283.
Behl et al., "Shape-memory polymers," Mater. Today, vol. 10 (2007) 20-28.
Gonzalo et al., "Synthesis, Characterization, and Thermal Properties of Piezoelectric Polyimides," J. Polym. Sci. Part A: Polym. Chem., vol. 47 (2009) 722-730.
Hamciuc et al., "Aromatic polyimides containing polar nitrile groups," Revue Rourmaine de Chimie, vol. 51 (2006) 765-771.
Hamciuc et al., "Study of thin films made from poly(amide-imide)s containing nitrile groups," Int'l . Semicond. Conf., vol. 2 (2010) 341-344.
Hamciuc et al., "Hybrid films based on a polyimide containing nitrile groups and barium and titanium oxides," High Perf. Polym., vol. 22 (2010) 225-236.
Hamciuc et al., "Aromatic poly(ether imide)s containing nitrile groups," High Perf. Polym., vol. 21 (2009) 205-218.
Hergenrother, "Recent Developments in High Temperature Organic Polymers," Polyimides and Other High-Temperature Polymers, Abadie, M.J.M. and Sillion, B., Eds., Elsevier: New York, 1991, pp. 1-18.
Jacobs et al., "Dielectric characteristics of polyimide CP2," Polym., vol. 51 (2010) 3139-3146.
Jeong et al., "Adhesion property of novel polyimides containing fluorine and phosphine oxide moieties," J. Adh. Sci. Technol., vol. 15 (2001) 1787-1803.
Kang et al., "Synthesis and characterization of polyimides from unsymmetrical diamine with cyano groups," Polym. J., vol. 33 (2001) 284-289.
Klein et al., "Synthesis and characterization of polyimides derived from cyano-containing 1,4-bis(4-aminophenoxy) benzene monomers," Polym. Bull., vol. 59 (2007) 1-12.
Georgiev et al., "Polyimide coatings containing azo-chromophores as structural units," J. Physics Conf. Ser., vol. 113 (2008) 012032.
Koerner et al., "Polymer design for high temperature shape memory: low crosslink density polyimides," Polymer, vol. 54 (2013) 391-402.
Koton et al, "Polyimides containing different heterocyclic unites in the main chain," Chem. Abstr. 20532k, vol. 96 (1982).
Koton et al, "Polyimides containing various heterocyclic main-chain units," Polym. Sci., vol. 23 (1981) 1909-1915.
Lee et al., "Enhancement of photogenerated mechanical force in azobenzene-functionalized polyimides," Angew. Chem., vol. 124 (2012) 4193-4197.
Li et al., "Synthesis and characterization of new polyimides containing nitrile groups," High Perf. Polym., vol. 17 (2005) 135-147.
Liaw et al., "High glass transitions of new polyamides, polyimides, and poly(amide-imide)s containing a triphenylamine group: synthesis and characterization," Macromol., vol. 35 (2002) 4669-4676.
Liaw et al., "Novel organosoluble poly(pyridine-imide) with pendent pyrene group: synthesis, thermal, optical, electrochemical, electrochromic, and protonation characterization," Macromol., vol. 40 (2007) 3568-3574.
Liaw et al., "Novel poly(pyridine imide) with pendent naphthalene groups: synthesis and thermal, optical, electrochemical, electrochromic, and protonation characterization," J. Polym. Sci. Part A: Polym. Chem., vol. 45 (2007) 2367-2374.
Machine, Translation of WO 2009/013376 as provided by WIPO Patentscope, Powered by Google Translate, accessed on Sep. 30, 2014.
Machine, Translation of JP 2005-023151 as provided by Patent Abstracts of Japan, accessed on Oct. 6, 2014.
Lee et al., "Photomechanical response of composite structures built from azobenzene liquid crystal polymer networks," Polymers, vol. 3 (2011) 1447-1457.
Sakamoto et al., "Highly polarized polymer-based light-emitting diodes fabricated by using very thin photoaligned polyimide layers," J. Appl. Phys., vol. 107 (2010) 113108.
Sakamoto et al., "Light exposure dependence of molecular orientation of glassy polyfluorene layers formed on photo-aligned polyimide films," Colloids Surf. B: Bioint., vol. 56 (2007) 260-264.
Mercer et al., "Synthesis and properties of new alternating copolyethers containing pendent cyano groups," Polym., vol. 34 (1994) 5355-5363.
Ounaies et al., "Structure-property study of piezoelectricity in polyimides," Proc. SPIE, vol. 3669 (1999) 171-178.
Park et al., "In situ poling and imidization of amorphous piezoelectric polyimides," Polym., vol. 45 (2004) 5417-5425, as provided in ICASE Report No. 2002-39.
Rabani et al., "Synthesis and characterization of two shape-memory polymers containing short aramid hard segments and poly(e-caprolactone) soft segments," Polymer, vol. 47 (2006) 4251-4260.

(56) References Cited

OTHER PUBLICATIONS

Saxena et al., "Synthesis and characterization of polyamides and poly(amide-imide)s derived from 2,6-bis(3-aminophenoxy)benzonitrile or 2,6-bis(4-aminophenoxy)benzonitrile," Polym. Int'l., vol. 54 (2005) 544-552.
Schuh et al., "Shape-memory properties of segmented polymers containing aramid hard segments and polycaprolactone soft segments," Polymers, vol. 2 (2010) 71-85.
Shumaker et la., "Synthesis of high temperature polyaspartimide-urea based shape memory polymers," Polymer, vol. 53 (2012) 4637-4642.
Sinou et al., "Synthesis of family of triarylphosphanes with fluorous phase affinity," Eur. J. Org. Chem., vol. (2002) 269-275.
Young et al., "Molecular modeling of the poling of piezoelectric polyimides," Polym., vol. 40 (1999) 2787-2795.
Tyan et al., "Effect of reactivity of organics-modified montmorillonite on the thermal and mechanical properties of montmorillonite/polyimide nanocomposites," Chem. Mater., vol. 13 (2001) 222-226.
Usami et al., "Improvement in photo-alignment efficiency of azobenzene-containing polyimide films," Thin Solid Films, vol. 518 (2009) 729-734.
Usami et al., "Pretilt angle control of liquid crystal molecules by photoaligned films of azobenzene-containing polyimide with a different content of side-chain," J. Appl. Phys., vol. 104 (2008) 113528.
United States Patent and Trademark Office, Non-Final Office Action in U.S. Appl. No. 13/661,194, mailed Jul. 2, 2014, 7 pages total.
United States Patent and Trademark Office, Non-Final Office Action in U.S. Appl. No. 14/013,090, mailed Aug. 22, 2014, 9 pages total.
Wang et al., "High-temperature dielectric polyimide films for energy storage applications," MRS Online Proc. Lib., vol. 1541 (2013) 6 pages total.
Wang et al., "Synthesis of symmetric and asymmetric polyimides containing benzonitrile groups for dielectric applications," Polym. Prints, vol. 51 (2010) 522-533.
Wang et al., "Synthesis and characterization of unsymmetrical benzonitrile-containing polyimides: viscosity-lowering effect and dielectric properties," J. Polym. Sci. Part A: Polym. Chem., vol. 51 (2013) 4998-5100.
Whitaker et al., "Synthesis and solid-state structure of substituted arylphosphine oxides," J. Org. Chem., vol. 60 (1995) 3499-3508.
Xie "Recent advances in polymer shape memory," Polymer, vol. 52 (2011) 4985-5000.
United States Patent and Trademark Office, Final Office Action in U.S. Appl. No. 13/661,194, mailed Dec. 11, 2014, 6 pages total.
Usami, K, et al., "Improvement in photo-alignment efficiency of azobenzene-containing polyimide films," Thin Solid Films 2009, 518, 729-734.
Usami, Kiyoaki, et al., "Pretilt Angle Control of Liquid Crystal Molecules by Photoaligned Films of Azobenzene-Containing Polyimide with Different Content of Side-Chain," Journal of Applied Phyics 104, 113528 (2008).
Lee, Kyung Min, and White, Timothy J., "Photomechanical Response of Composite Structures Built from Azobenzene Liquid Crystal Polymer Networks," Polymers (2011), 3, 1447-1457.
Georgiev, A., et al, "Polyimide Coatings Containing Azo-Chromophores as Structural Units," Journal of Physics, Conference Series vol. 113 No. 1 (2008) 012032.
Sakamoto, Kenji, et al., "Highly Polarized Polymer-Based Light Emitting Diodes Fabricated by Using Very Thin Photoaligned Polyimide Layers," Journal of Applied Physics 107, 113108 (2010).
Sakamoto, Kenji, et al., "Light Exposure Dependence of Molecular Orientation of Glassy Polyfluorene Layers Formed on Photo-Aligned Polyimide Films," Colloids and Surfaces B: Biointerfaces 56, pp. 260-264 (2007).
Usami, K., et al., "Stability of Photo-Induced Alignment of Azobenzene-Containing Polyimides," Molecular Crystals and Liquid Crystals (2005) 438:1, 227/[1791]-236[1800].
Park, B., et al., "Thermal and Optical Stabilities of Photoisomerizable Polyimide Layers for Nematic Liquid Crystal Alignments," Jpn. J. Appl. Phys. vol. 37 (1998) pp. 5663-5668.
Cain, J. C., "Para- and Meta-nitrosoacetanilide," J. Chem. Soc., Trans. 1908, 93, 681-684.
Yu, Y., et al., "Precisely Direction-Controllable Bending of Cross-Linked Liquid-Crystalline Polymer Films by Light," Mol. Cryst. Liq. Cryst., vol. 436, pp. 281/[1235]-290/[1244], 2005.
Si, J., et al., "Thermosetting enhancement of the light-induced polar orientation stability of molecules in polymers," J. Appl. Phys. 85, 8018 (1999); doi: 10.1063/1.370637.
Eisenbach, C. D., "Relation between Photochromism of Chromophores and Free Volume Theory in Bulk Polyers," Ber. Bunsenges. Phys. Chem. 1980, 84, 680.
Pieroni, O., et al., "Photoresponsive Polymeric Materials," Trends Polym. Sci. (Cambridge, U.K.) 1995, 3, 282-287.
Mathisen, R., et al., "Imidization studies of polyamic acids by dye-labeling technique," Polymer Preprints (American Chemical Society, Division of Polymer Chemistry) (1987), 28(1), 82-83.
Hergenrother, P.M., "Recent Developments in High Temperature Organic Polymers," Polyimides and Other High-Temperature Polymers, Abadie, M.J.M. and Sillion, B., Eds., Elsevier: New York, 1991, pp. 1-18.
Yager, K. G., et al., "Azobenzene Polymers as Photomechanical and Multifunctional Smart Materials," Intelligent Materials, Shahinpoor, M. and Schneider, H.-J., Eds., Royal Society of Chemistry: Cambridge, UK, 2008; pp. 424-446.
Irie, M, et al., "Photoresponsive Polymers," Functional Monomers and Polymers, 2nd ed., Takemoto, K., et al., Eds., Dekker: New York, 1997, pp. 65-116.
Tan, Loon-Seng, et al., U.S. Appl. No. 13/557,326, filed Jul. 25, 2012.
Tan, Loon-Seng, et al., U.S. Appl. No. 13/546,439, filed Jul. 11, 2012.
Tan, Loon-Seng, et al., U.S. Appl. No. 13/661,194, filed Oct. 26, 2012.
U.S. Patent and Trademark Office, Non-Final Office Action mailed Feb. 10, 2014, U.S. Appl. No. 13/866,551, 5 pages.

\* cited by examiner

MULTI(AZOBENZENE-AMINE) PHOTOACTIVE CROSSLINKERS AND METHODS OF MAKING THE SAME

CROSS-REFERENCE TO RELATED APPLICATIONS

This application claims the benefit of U.S. Provisional Patent Application No. 61/636,134, filed on Apr. 20, 2012, by inventor Loon-Seng Tan, et al., entitled "Multi(Azobenzene-Amine) Photo-Active Crosslinkers," and U.S. Provisional Patent Application No. 61/636,170, filed Apr. 20, 2012, by inventor Loon-Seng Tan, et al., entitled "Azobenzene-Containing Glassy Polyimides Capable of Photo-Induced Large-Angle Bending," both of which are incorporated herein by reference in their entirety.

RIGHTS OF THE GOVERNMENT

The invention described herein may be manufactured and used by or for the Government of the United States for all governmental purposes without the payment of any royalty.

BACKGROUND OF THE INVENTION

1. Field of the Invention

The present invention relates to a new multi(azobenzene-amine) cross-linker and its derivatives that are used to crosslink imide-based, photomechanical polymers derived from an aromatic amine and an aromatic dianhydride.

2. Description of the Related Art

Photomechanical polymers are a special class of smart (stimuli-responsive) polymers that are responsive to light and are capable of generating photo-directed motions and dimensional or shape alteration at the macro-scale level. These motions and/or alterations are driven by the collective molecular-volume change brought about by the chromophoric units upon appropriate irradiation. The chromophoric units in photoresponsive polymers are photochromic and have the unique ability to reversibly interconvert between two structural isomers (each with distinctly different optical and physical properties) under appropriate excitation conditions. Examples of chromophoric units can be found in photo-isomerizable molecules such as azobenzenes, spiropyrans, spirooxazines, diarylethylenes, and fulgides. However, with respect to photomechanical polymers, azobenzene is the most commonly used molecularly-actuating moiety because of its excellent thermal stability and resolved isomeric forms, as well as its ability to form surface gradient reliefs when subjected to conventional or polarization holography.

The resulting photomechanical output of a polymeric material depends not only on its optical properties (absorption wavelength, wavelength of exposure, polarization of exposure), but also on its molecular architecture and morphology (amorphous, crystalline, liquid crystalline). In addition, the photomechanical output is dependent on the polymeric material's thermomechanical properties, as well as the geometrical properties of the device, e.g. thickness of a cantilever.

Polyimides (PIs) represent an important class of heat-resistant polymers that have found utility in a wide spectrum of applications, ranging from structural components to electronic and photonic devices. The widespread application of polyimides is mainly the result of their excellent combination of physical properties, thermal stability, and processability. For example, polyimides containing azobenzene in the backbone or side-chain have been investigated for photo-induced alignment in liquid crystal display (LCD) as well as nonlinear optical applications. More recently, an azobenzene-containing poly(amic acid) (a PI precursor) was crosslinked by a triamine in N,N-dimethylformamide (DMF) and the resulting sol-gels showed a two-fold increase in the storage modulus after irradiation with 405 nm light. Another closely related aromatic poly(amic acid) was reported to be photomechanically active.

SUMMARY OF THE INVENTION

In accordance with the present invention, there are provided photo-active, multi-(azobenzene-amine) cross-linkers derived from a tris(azobenzene)-containing compound. The presently disclosed cross-linkers exhibit the following general structure in which, for meta-azo substitution (with reference to ether-oxygen), R=H, and for para-azo substitution, R=H, F, Cl, $CF_3$, $CH_3$:

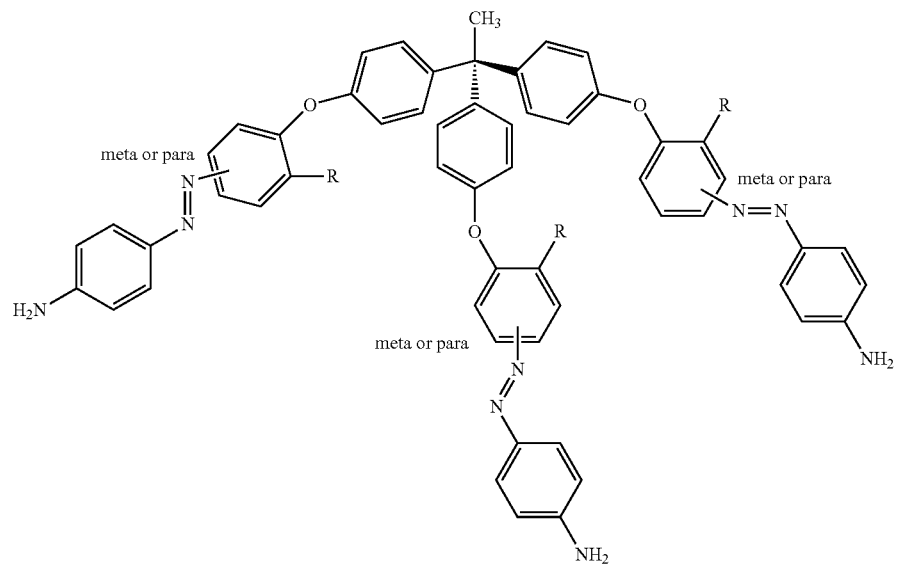

The present invention further includes a method for making the above shown tris(azobenzene-amine) cross-linker comprising the steps of: providing 1,1,1,-tris(4-hydroxyphenyl)ethane; treating the 1,1,1,-tris(4-hydroxyphenyl)ethane with a nitro-activated aryl halide in presence of potassium carbonate to produce a tris[(nitrophenoxy)phenyl]ethane compound; reducing the tris[(nitrophenoxy)phenyl]ethane compound to a tris[(acetamidophenoxy)phenyl]ethane compound by catalytic hydrogenation; treating the tris[(acetamidophenoxy)phenyl]ethane compound with 4-nitrosoacetanilide in acetic acid to yield a tris(azobenzene-amide) compound; and converting the amide to amine in the tris (azobenzene-amide) compound via an alkaline deacetylation reaction.

In one embodiment of the method, the nitro-activated aryl halide is 1-fluoro-4-nitrobenzene and the tris[(nitrophenoxy)phenyl]ethane compound is 1,1,1-tris[4-(4-nitrophenoxy)phenyl]ethane. In another embodiment, the nitro-activated aryl halide is 1,2-difluoro-4-nitrobenzene and the tris[(nitrophenoxy)phenyl]ethane compound is 1,1,1-tris[4-(4-nitrophenoxy)phenyl]ethane. In another embodiment, the nitro-activated aryl halide is 2-chloro-1-fluoro-4-nitrobenzene, and the tris[(nitrophenoxy)phenyl]ethane compound is 1,1,1-tris[4-(4-nitrophenoxy)phenyl]ethane. In an alternative embodiment of the method, the nitro-activated aryl halide is 1-fluoro-4-nitro-2-(trifluoromethyl)benzene, and the tris[(nitrophenoxy)phenyl]ethane compound is 1,1,1-tris[4-(4-nitrophenoxy)phenyl]ethane. In a further embodiment, the nitro-activated aryl halide is 1-fluoro-2-methyl-4-nitrobenzene, and the tris[(nitrophenoxy)phenyl]ethane compound is 1,1,1-tris[4-(4-nitrophenoxy)phenyl]ethane.

DETAILED DESCRIPTION

Figure 1:
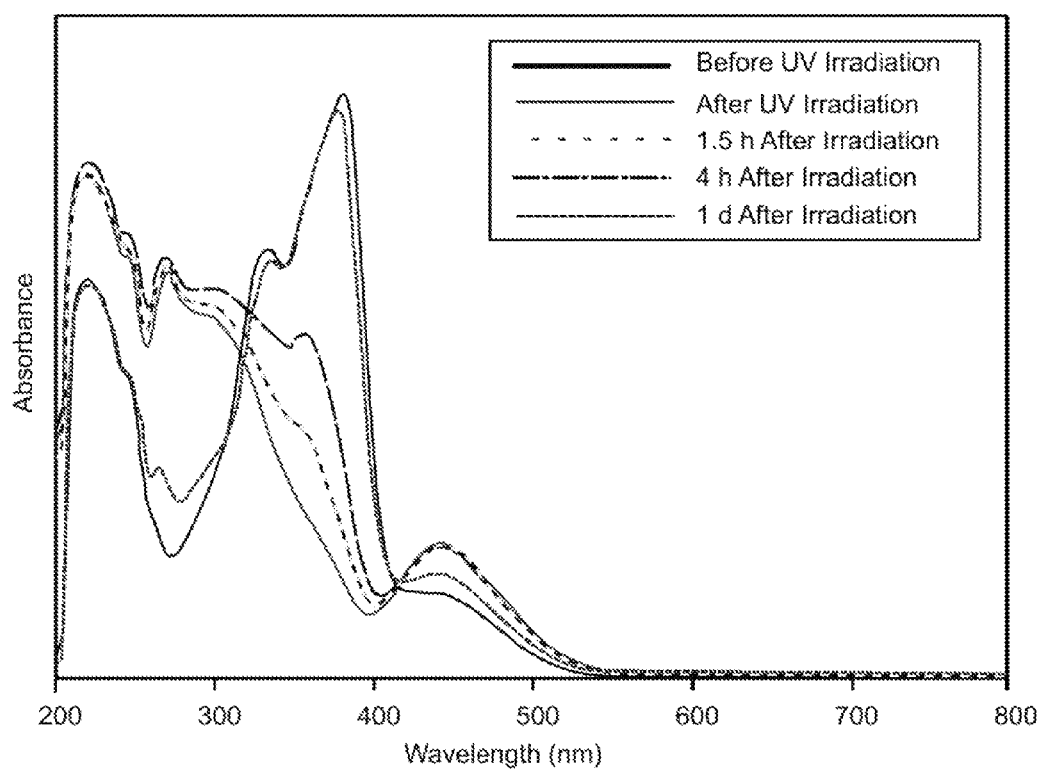
FIG. 1 is an UV-vis spectra of model tris(azobenzene-N-phthalimide)/THF solution before and after the irradiation of UV lamp (366 nm, 10 min), in accordance with an embodiment of the invention.

It has been estimated that the mechanical work per polymer chain based on the azobenzene isomerization process is only 10% efficient, meaning that only 10% of the incident photon energy ($4 \times 10^{-19}$ J) is converted to mechanical work (~$4.5 \times 10^{-20}$ J). As a way to improve the transduction efficiency via increasing the effective number density of azobenzene-actuating units in a polyimide (PI) network structure, the presently disclosed crosslinker is designed to contain three azobenzenes per molecule, via a trifunctional monomer, which can promote polyimide network formation under appropriate fabricating and curing conditions.

A photo-active, multi-(azobenzene-amine) crosslinker derived from a tris(azobenzene)-containing compound according to the present invention exhibits the following generic structure in which, for meta-azo substitution (with reference to ether-oxygen), R=H, and for para-azo substitution, R=H, F, Cl, $CF_3$, $CH_3$:

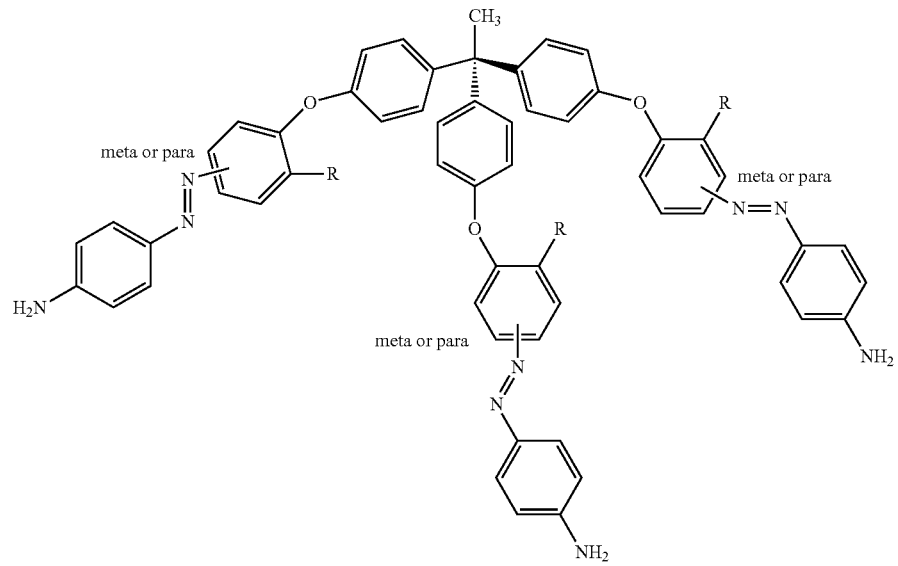

The present invention further includes a method for making the above shown tris(azobenzene-amine) cross-linker comprising the steps of: providing 1,1,1,-tris(4-hydroxyphenyl)ethane; treating the 1,1,1,-tris(4-hydroxyphenyl)ethane with a nitro-activated aryl halide such as 1-fluoro-4-nitrobenzene, 1,2-difluoro-4-nitrobenzene, 2-chloro-1-fluoro-4-nitrobenzene, 1-fluoro-4-nitro-2(trifluromethyl)benzene or 1-fluoro-2-methyl-4-nitrobenzene) in presence of potassium carbonate to produce a tris[(nitrophenoxy)phenyl]ethane compound; reducing the tris[(nitrophenoxy)phenyl]ethane compound to a tris[(acetamidophenoxy)phenyl]ethane compound by catalytic hydrogenation; treating the tris[(acetamidophenoxy)phenyl]ethane compound with 4-nitrosoacetanilide in acetic acid to yield a tris(azobenzene-amide) compound; and converting the amide to amine in the tris (azobenzene-amide) compound via an alkaline deacetylation reaction.

In various embodiments of the method, the nitro-activated aryl halide may comprise 1-fluoro-4-nitrobenzene; 1,2-difluoro-4-nitrobenzene; 2-chloro-1-fluoro-4-nitrobenzene; 1-fluoro-4-nitro-2-(trifluoromethyl)benzene; or 1-fluoro-2-methyl-4-nitrobenzene. In another embodiment of the method, the tris[(nitrophenoxy)phenyl]ethane compound may comprise 1,1,1-tris[4-(4-nitrophenoxy)phenyl]ethane.

As an example, a representative synthesis of a photo-active, multi-(azobenzene-amine) cross-linker according to the present invention (compound 6) is shown in Scheme 1 below.

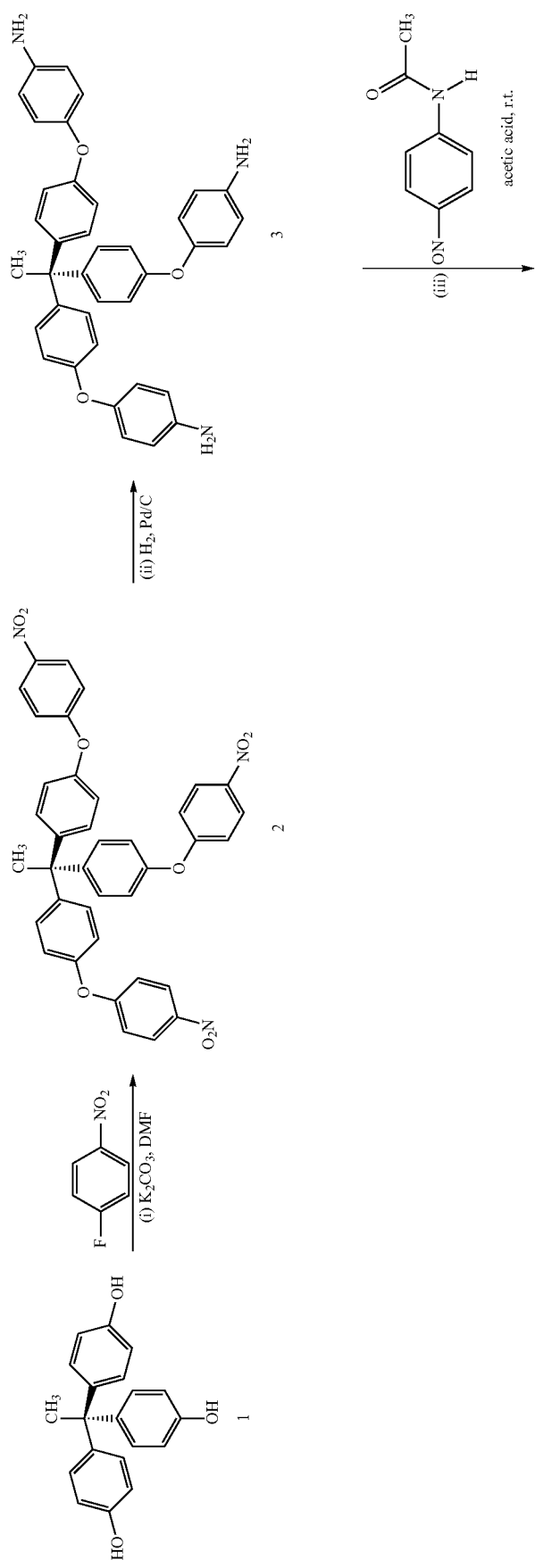
Scheme 1. Synthesis of a tris(azobenzene-amine) monomer (6) and tris(N-phthalimide)-endcapped model compound (7).

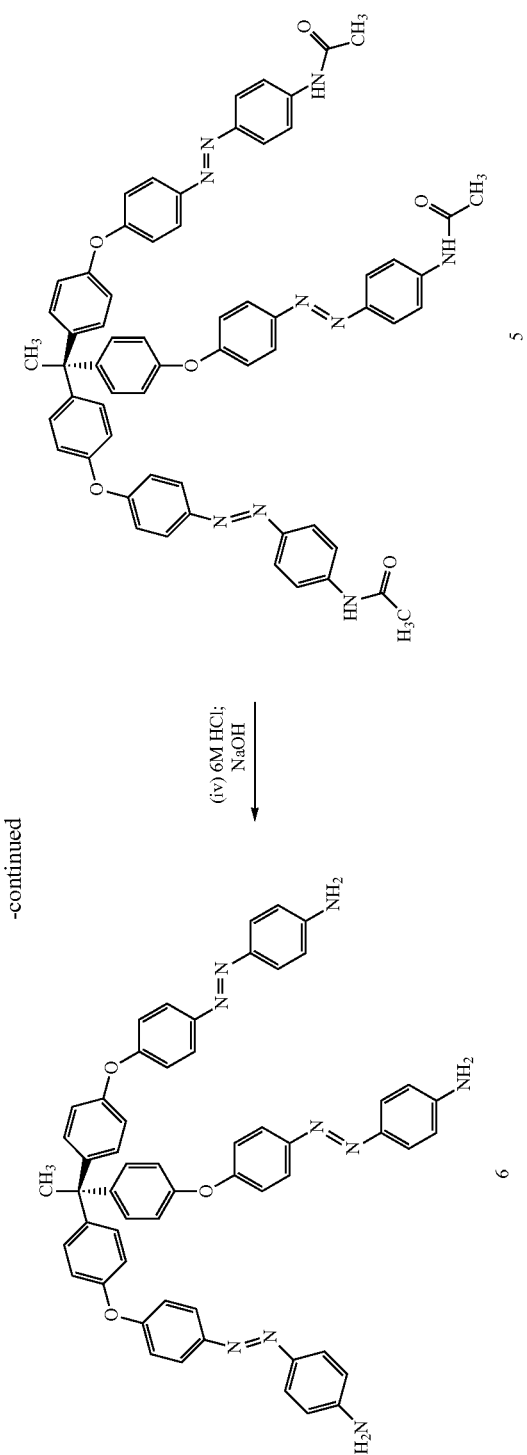

In Scheme 1, 1,1,1,-tris(4-hydroxyphenyl)ethane (compound 1) was treated with 1-fluoro-4-nitrobenzene in presence of potassium carbonate to make 1,1,1-tris[4-(4-nitrophenoxy)phenyl]ethane (compound 2), which was reduced to 1,1,1-tris[4-(4-aminophenoxy)phenyl]ethane (compound 3) by catalytic hydrogenation. The reaction of compound 3 and 4-nitrosoacetanilide (compound 4) in acetic acid yielded the tris(azobenzene-amide) as compound 5. The tris(azobenzene-amine) monomer (compound 6) was generated after the deprotection of compound 5 via alkaline deacetylation reaction. By end-capping compound 6 with phthalic anhydride, a tris(azobenzene-N-phthalimide) model compound (compound 7) was obtained (see Scheme 1 above), which was useful in validating and semi-quantifying the kinetics of photoisomerization process in the cross-linked azo-polyimide system.

The following examples and methods are presented as illustrative of the present invention or methods of making or carrying out the invention and are not restrictive or limiting of the scope of the invention in any manner. The tris(azobenzene-amine) crosslinkers and the crosslinked, azobenzene-containing polyimides according to the present invention may be synthesized following the procedures given in the following examples.

EXAMPLE 1

Synthesis of
1,1,1-Tris[4-(4-nitrophenoxy)phenyl]ethane

Into a 250 mL three-necked flask equipped with a magnetic stir bar and nitrogen inlet and outlet were placed 1,1,1,-tris (4-hydroxyphenyl)ethane (10.0 g, 33.0 mmol), 1-fluoro-4-nitrobenzene (15.4 g, 109 mmol), potassium carbonate (15.1 g, 109 mmol) and DMF (100 mL). The mixture was stirred at room temperature for 24 hours and filtered. The filtrate was diluted with ethyl acetate (400 mL) and the organic layer was separated. The organic layer was washed with water 3 times. It was dried over anhydrous magnesium sulfate and filtered. The filtrate was concentrated to 75 mL on a rotary evaporator, and then stored in refrigerator for several days to afford 11.2 g (51%) of off-white crystals, m.p. 98-99° C. MS (m/e): 669 ($M^+$). Anal. Calcd. for $C_{38}H_{27}N_3O_9$: C, 68.18%; H, 4.06%; N, 6.27%; O, 21.50%. Found: C, 67.69%; H, 4.26%; N, 6.21%; O, 21.22%. FT-IR (KBr, $cm^{-1}$): 3076, 2979, 1586, 1513, 1486, 1344, 1248, 1165, 1107, 874, 846. $^1$H-NMR (DMSO-$d_6$, δ in ppm): 2.26 (s, 3H, $CH_3$), 7.17-7.27 (m, 18H, Ar—H), 8.28-8.31 (d, 6H, Ar—H).

EXAMPLE 2

Synthesis of
1,1,1-Tris[4-(4-aminophenoxy)phenyl]ethane 1,1,1-Tris[4-(4-nitrophenoxy)phenyl]ethane (Example 1; 3; 5.0 g, 7.5 mmol), THF (50 mL) and 5% palladium on activated carbon (0.50 g) were added to a hydrogenation bottle. The bottle was secured on a Parr hydrogenation apparatus, flushed three times with hydrogen, and then pressurized to 55 psi. After the mixture had been agitated at room temperature for 24 hours under the hydrogen pressure of 55 psi, it was filtered through Celite. The filter cake was washed with THF, and then the filtrate was evaporated to dryness on a rotary evaporator to afford a 4.25 g (98%) of yellow crystal, which was used without further purification, m.p. 220-221° C. MS (m/e): 579 ($M^+$). Anal. Calcd. for $C_{38}H_{33}N_3O_3$: C, 78.73%; H, 5.74%; N, 7.25%. Found: C, 78.17%; H, 5.78%; N, 7.04%. FT-IR (KBr, $cm^{-1}$): 3441, 3361 ($NH_2$), 3035, 2970, 1617, 1581, 1497, 1384, 1232, 1173, 1117, 1010, 871, 842. $^1$H-NMR (DMSO-$d_6$, δ in ppm): 2.02 (s, 3H, $CH_3$), 4.99 (s, 6H, $NH_2$), 6.53-6.58 (d, 6H, Ar—H), 6.68-6.74 (m, 12H, Ar—H), 6.88-6.93 (d, 6H, Ar—H).

EXAMPLE 3

Synthesis of N-(4-nitrosophenyl)acetamide

After oxone (potassium peroxymonosulfate, from Sigma-Aldrich®; 12.28 g, 20.0 mmol) had dissolved completely in water (100 mL), potassium carbonate (4.14 g, 30 mmol) was added slowly to neutralize the solution to a weak acidity. The solution was added quickly into a solution of 4'-aminoacetanilide (from Sigma-Aldrich®; 1.50 g, 10.0 mmol) in water (150 mL). The mixture immediately turned green, and greenish-gray solids started to fall out of solution. After the mixture had been stirred for another 10 minutes, the precipitates were collected on a filter funnel, air dried, and recrystallized from hot ethanol. Two batches of products were collected to give a total yield of 1.06 g (65%) greenish crystals, mp 179-180° C. (lit. 179-180° C.).

EXAMPLE 4

Synthesis of
1,1,1-tris{4-[4-(4-acetamidophenyldiazenyl)
phenoxy]phenyl}ethane 1,1,1-Tris(4-(4-aminophenoxy)phenyl)ethane (Example 2; 0.580 g, 1.00 mmol), N-(4-nitrosophenyl)acetamide (Example 3; 0.985 g, 6 mmol) and acetic acid (20 mL) were charged into a 150 mL round-bottomed flask equipped with a magnetic stir bar. The mixture was stirred at room temperature for 48 hours. The mixture was at first turned into a greenish solution, and then yellow particles started to precipitate out of the solution. The mixture was diluted by deionized water (100 mL). Solids were collected and washed with water (500 mL), followed by ethanol (200 mL) to remove most of the unreacted nitroso reagent. The solid was then extracted by hot acetone (100 mL) four times. The acetone extract was concentrated on a rotary evaporator to give yellow solids as raw product. The raw product was slurried in hot ethanol (50 mL) and filtered twice after cooling to room temperature in between to give 0.62 g (61%) of yellow solids, mp 220° C. (dec.). $^1$H-NMR ($d_6$-DMSO, δ in ppm): 2.09 (s, 9H, $COCH_3$), 2.15 (s, 3H, $CCH_3$) 7.03-7.15 (m, 18H), 7.79-7.87 (m, 18H) 10.28 (s, 3H, NHCO). $^{13}$C-NMR ($d_6$-DMSO, δ in ppm): 24.16, 30.28, 51.00, 118.50, 118.86, 119.18, 123.42, 124.35, 129.99, 142.09, 144.50, 147.38, 147.77, 153.78, 159.07, 168.06.

EXAMPLE 5

Synthesis of 1,1,1-tris{4-[4-(4-aminophenyldiazenyl)
phenoxy]phenyl}ethane

To a 100 mL round-bottomed flask with a stir-bar and a condenser, 1,1,1-tris[4-(4-(4-acetamidophenyldiazenyl)phenoxy)phenyl]ethane (Example 4; 0.50 g, 0.49 mmol), 6 M HCl (20 mL) and 95% ethanol (20 mL) were charged and heated to 80° C. The mixture was stirred at 80° C. for 3 days. After the mixture was allowed to cool to room temperature, water (60 mL) added. The resulting red solid was collected by filtration and washed with dilute sodium bicarbonate solution, followed by deionized water (300 mL). After being air dried, the crude product was purified by column chromatography (silica gel, ethyl acetate as eluent). The solvent was removed by a rotary evaporator to afford 0.23 g (52.5%) of orange red solid, mp >300° C. MS (m/e): 892 (M$^+$). Anal. Calcd. for $C_{56}H_{45}N_9O_3$: C, 75.40%; H, 5.08%; N, 14.13%. Found: C, 75.44%; H, 5.08%; N, 13.98%. $^1$H-NMR (d$_6$-DMSO, δ in ppm): 2.12 (s, 3H, CCH$_3$), 6.03 (s, 6H, NH$_2$), 6.67-6.70 (d, 6H, J=8.7 Hz), 6.99-7.02 (d, 6H, J=8.7 Hz), 7.09-7.13 (m, 12H), 7.62-7.66 (d, 6H, J=8.7 Hz), 7.75-7.78 (d, 6H, J=8.7 Hz). $^{13}$C-NMR (d$_6$-DMSO, δ in ppm): 30.34, 51.91, 113.41, 118.44, 118.69, 123.52, 124.96, 129.93, 142.92, 144.25, 148.41, 152.56, 154.21, 157.75.

EXAMPLE 6

Synthesis of 1,1,1-Tris{4-[4-(4-phthalimidophenyldiazenyl) phenoxy]phenyl}ethane (Model Compound)

Into a 250 mL three-necked flask equipped with a magnetic stir bar and nitrogen inlet and outlet were placed 1,1,1-tris{4-[4-(4-aminophenyldiazenyl)phenoxy]phenyl}ethane (Example 5; 0.892 g, 1.00 mmol), phthalic anhydride (0,444 g, 3.00 mmol) and acetic acid (20 mL). The mixture was stirred under refluxing for 14 hours and allowed to cool to room temperature. The precipitate was collected by filtration and dried in an oven to afford 0.96 g (75%) of orange powder, mp >300° C. MS (m/e): 1282 (M$^+$). Anal. Calcd. for $C_{80}H_{51}N_9O_9$: C, 74.93%; H, 4.01%; N, 9.83%. Found: C, 75.00%; H, 4.11%; N, 9.44%. $^1$H-NMR (d$_6$-DMSO, δ in ppm): 2.21 (s, 3H, CCH$_3$), 7.08-7.13 (d, 6H, Ar—H), 7.19-7.21 (dd, 12H, Ar—H), 7.67-7.71 (d, 6H, Ar—H), 7.87-8.03 (m, 24H, Ar—H).

EXAMPLE 7

Representative Procedure for the Synthesis of Azobenzene-Containing Polyimides (20 Mol %)

1,3-Bis(3-aminophenoxy)benzene (APB; 0.4093 g, 1.400 mmol) and DMAc (8 mL) were added to a 50 mL 3-necked flask equipped with a magnetic stirrer and a nitrogen inlet and outlet and stirred under dry nitrogen at room temperature for 30 minutes. 2,2-Bis(phthalic anhydride)-1,1,1,3,3,3-hexafluoroisopropane (6FDA; 0.8885, 2.000 mmol) was then introduced to the resulting solution. The light yellow solution was agitated at room temperature for 24 hours to afford a poly (amic acid) solution. Then, the tris(azobenzene-amine) cross-linker (Example 5; 0.3568 g, 0.400 mmol) was added to this solution. After the crosslinker had completely dissolved in DMAc, the mixture was poured into a glass petri dish, followed by vacuum evaporation of DMAc at 50° C., and heat-treated according to following schedule: 100° C./2 hrs, 150° C./2 hrs, 175° C./1 hr, 200° C./2 hrs, 250° C./1 hr and 300° C./1 hr to form polyimide films. The film thickness was approximately 20 μm. To prepare a polyimide with (ax100) mol % of the crosslinker, this procedure was followed with variation in the mole ratio of APB:6FDA:Crosslinker=(1−3a/2):1:a, where a can be varied from 0.05 to 0.50.

EXAMPLE 8

UV-Vis Spectroscopic Study of Photo-Isomerization of Model Compound

The reversible trans-cis photoisomerization of the model compound (i.e compound 7 in Scheme 1; also see Example 6) was investigated in THF solution. After irradiation with a 366 nm UV-lamp for 10 minutes, the compound's UV absorption band at 383 nm disappeared, indicating that all the trans-isomers were converted into cis-isomers. At the same time, the absorbance at 443 nm, which corresponds to cis-isomers, increased to a maximum. After the UV-irradiation and having been placed on a lab bench, the cis-isomers underwent thermally activated cis-trans isomerization and the absorption peak of trans-isomers were totally recovered in 2 days (FIG. 1).

Figure 2:
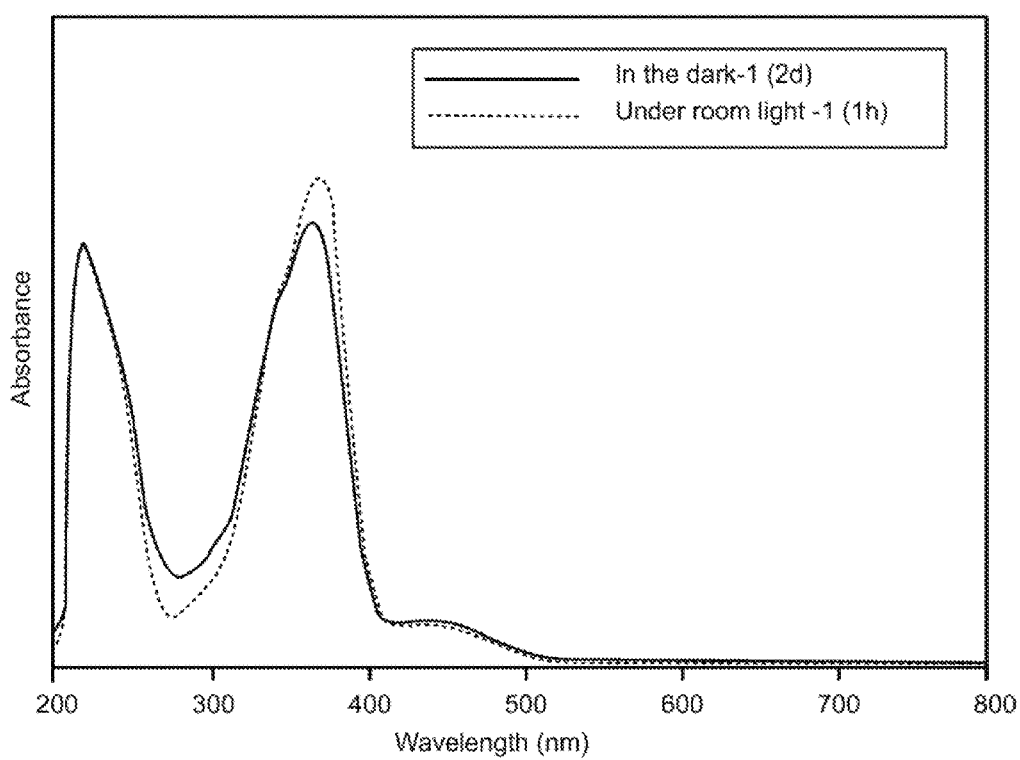
FIG. 2 is an UV-vis spectra of model tris(azobenzene-N-phthalimide)/THF solution under the room light and in the dark intermittently in accordance with an embodiment of the invention.

Interestingly, even the room light can convert trans-azobenzene units in the model compound to cis-conformations partially in 1 hour (FIG. 2). After its THF solution was stored in the dark for 2 days, the cis-azobenzenes fully reverted back to the trans-conformations. The trans-cis-trans cycles could be repeated several times at room temperature, indicating relatively low-energy barrier for the equilibration of isomers.

Although specific embodiments have been described in detail in the foregoing description and illustrated in the drawings, various other embodiments, changes, and modifications to the disclosed embodiment(s) will become apparent to those skilled in the art. All such other embodiments, changes, and modifications are intended to come within the spirit and scope of the appended claims.

What is claimed is:
1. A tris(azobenzene-amine) cross-linker with the following structure:

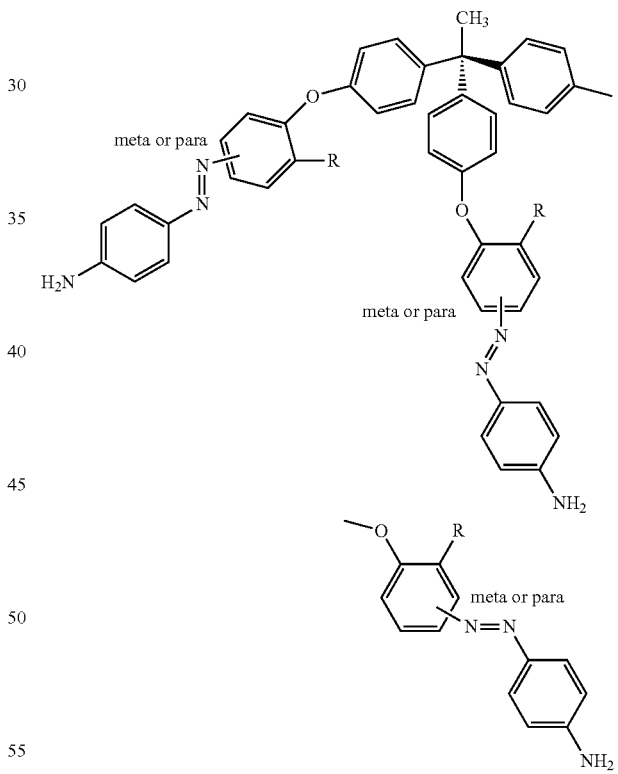

wherein for meta-azo substitution, R is equal to H, and for para-azo substitution, R is selected from the group consisting of H, F, Cl, CF$_3$, and CH$_3$.

2. A method for making the tris(azobenzene-amine) cross-linker of claim 1 comprising the steps:
providing 1,1,1,-tris(4-hydroxyphenyl)ethane;
treating the 1,1,1,-tris(4-hydroxyphenyl)ethane with a nitro-activated aryl halide in presence of potassium carbonate to produce a tris[(nitrophenoxy)phenyl]ethane compound;

reducing the tris[(nitrophenoxy)phenyl]ethane compound to a tris[(acetamidophenoxy)phenyl]ethane compound by catalytic hydrogenation;

treating the tris[(acetamidophenoxy)phenyl]ethane compound with 4-nitrosoacetanilide in acetic acid to yield a tris(azobenzene-amide) compound; and converting amides in the tris(azobenzene-amide) compound to amines via an alkaline deacetylation reaction to form the tris(azobenzene-amine) cross-linker.

3. The method for making the tris(azobenzene-amine) cross-linker of claim 2 wherein the nitro-activated aryl halide is 1-fluoro-4-nitrobenzene and the tris[(nitrophenoxy)phenyl]ethane compound is 1,1,1-tris[4-(4-nitrophenoxy)phenyl]ethane.

4. The method for making the tris(azobenzene-amine) cross-linker of claim 2 wherein the nitro-activated aryl halide is 1,2-difluoro-4-nitrobenzene and the tris[(nitrophenoxy)phenyl]ethane compound is 1,1,1-tris[4-(4-nitrophenoxy)phenyl]ethane.

5. The method for making the tris(azobenzene-amine) cross-linker of claim 2 wherein the nitro-activated aryl halide is 2-chloro-1-fluoro-4-nitrobenzene, and the tris[(nitrophenoxy)phenyl]ethane compound is 1,1,1-tris[4-(4-nitrophenoxy)phenyl]ethane.

6. The method for making the tris(azobenzene-amine) cross-linker of claim 2 wherein the nitro-activated aryl halide is 1-fluoro-4-nitro-2-(trifluoromethyl)benzene, and the tris[(nitrophenoxy)phenyl]ethane compound is 1,1,1-tris[4-(4-nitrophenoxy)phenyl]ethane.

7. The method for making the tris(azobenzene-amine) cross-linker of claim 2 wherein the nitro-activated aryl halide is 1-fluoro-2-methyl-4-nitrobenzene, and the tris[(nitrophenoxy)phenyl]ethane compound is 1,1,1-tris[4-(4-nitrophenoxy)phenyl]ethane.

* * * * *